United States Patent [19]

Song et al.

[11] Patent Number: 5,035,884

[45] Date of Patent: Jul. 30, 1991

[54] METHYLENE PYRROLIDONE COPOLYMERS FOR CONTACT LENS AND PHARMACEUTICAL PREPARATIONS

[75] Inventors: Suk-Zu Song, Flanders; Surendra C. Mehta, Randolph; Kuchi S. Murthy, Morris Plains; Russell U. Nesbitt, Somerville; Mahdi B. Fawzi, Flanders, all of N.J.

[73] Assignee: Warner-Lambert Company, Morris Plains, N.J.

[21] Appl. No.: 480,431

[22] Filed: Feb. 15, 1990

Related U.S. Application Data

[62] Division of Ser. No. 347,630, May 5, 1989, Pat. No. 4,931,519, which is a division of Ser. No. 57,467, Jun. 2, 1987, Pat. No. 4,851,545.

[51] Int. Cl.$^5$ .................... A61K 31/785; G02C 7/04
[52] U.S. Cl. .................... 424/78; 351/160 R; 424/81; 424/430; 424/435; 424/436; 424/449; 523/106; 523/111
[58] Field of Search .............. 351/160 R; 424/78, 80, 424/81, 430, 435, 436, 449; 523/108, 106, 111

[56] References Cited

U.S. PATENT DOCUMENTS

| | | | |
|---|---|---|---|
| 3,452,015 | 6/1969 | Dillard | 544/335 |
| 3,479,327 | 11/1969 | Marijam | 540/485 |
| 3,542,778 | 11/1970 | Dillard | 544/335 |
| 4,593,053 | 6/1986 | Jevne | 523/111 |
| 4,866,148 | 9/1989 | Geyer | 523/108 |

FOREIGN PATENT DOCUMENTS

70/3307 5/1969 South Africa .

*Primary Examiner*—Christopher Henderson
*Attorney, Agent, or Firm*—Elizabeth M. Anderson

[57] ABSTRACT

A new series of copolymers which are useful as coatings for solid dosage forms, for transdermal devices, for wound dressing materials, and for contact lenses. Also disclosed are methods for preparing monomers and polymers as well as pharmaceutical compositions containing such polymers.

5 Claims, No Drawings

METHYLENE PYRROLIDONE COPOLYMERS FOR CONTACT LENS AND PHARMACEUTICAL PREPARATIONS

This is a divisional of U.S. application Ser. No. 347,630 filed May 5, 1989, now U.S. Pat. No. 4,931,510, which is a divisional of U.S. application Ser. No. 057,467 filed June 2, 1987, now U.S. Pat. No. 4,851,545 issued July 25, 1989.

BACKGROUND OF THE INVENTION

This invention relates to a new and useful series of monomers, homopolymers and copolymers. The copolymers have pharmaceutical applications. The copolymers provide a coating for solid dosage forms used for controlled release of pharmaceuticals. They also provide material for transdermal devices. The copolymers provide materials for wound dressings. The copolymers are also useful materials for soft contact lenses.

SUMMARY

One aspect of the present invention is a compound of the formula I

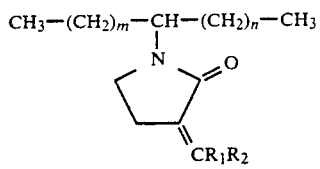

wherein m and n are each independently an integer of from 0 to 3, and $R_1$ and $R_2$ are each independently hydrogen, hydroxyl, or alkyl of from one to four carbon atoms.

Preferably m and n are each independently 0 or 1 and $R_1$ and $R_2$ are each independently hydrogen or methyl.

Most preferred is N-isopropyl-3-methylene-2-pyrrolidone.

Another aspect of the present invention is a homopolymer synthesized from the above monomer, formula I above, by a free radical polymerization reaction using azobisisobutyronitrile. The homopolymer has a molecular weight of from 500 to 20,000.

Another aspect of the present invention is a random copolymer formed from a new monomer, formula I above, together with 2-hydroxyethyl methacrylate and azobisisobutyronitrile. The ratios for the two are from 1 to 10 or from 10 to 1 depending upon the properties desired.

Yet another aspect of the present invention is a process for producing and purifying a monomer, producing a corresponding homopolymer, and producing a copolymer which swells but does not dissolve in water.

Still another aspect of the present invention is the use of the above copolymers as coating material for solid dosage forms for controlled release.

Another aspect of the present invention is the use of the above copolymers as wound dressings.

Another aspect of the invention is the use of the above copolymers in soft contact lenses.

Yet another aspect of the present invention is the use of the copolymer in transdermal devices.

Yet still another aspect of the present invention is a composition comprising a medicament and a copolymer.

DETAILED DESCRIPTION

A novel monomer of the present invention according to formula I as described above

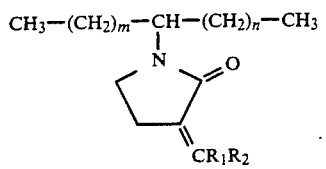

is prepared by refluxing an alkyl-2-pyrrolidone in a mixture of diethyl oxalate and sodium hydride to produce a solid, an adduct of alkyl-2-pyrrolidone with diethyl oxalate, which is then filtered and dried. The adduct is subsequently suspended in a reagent; paraformaldehyde is added to the suspension, and the resulting mixture is further treated by heating, cooling and filtering. CuCl is added to the filtrate which is then distilled. The monomer is produced in a ratio of about 2:1 to the starting material.

A preferred starting material is a compound of formula I above wherein m and n are each independently 0 or 1 and $R_1$ and $R_2$ are each hydrogen or an alkyl of from one to two carbon atoms or one of $R_1$ or $R_2$ is hydroxyl. One example of a preferred starting material is N-isopropyl-2-pyrrolidone. Generally refluxing this with a minimum of diethyl oxalate and sodium hydride occurs for from 10 to 30 hours, preferably from 20 to 26 hours. The resulting adduct is suspended in xylene or toluene; preferably in xylene. After further reaction the fraction is preferably distilled at from 55°–65° C. and about 0.3 mmHg.

The purification of the pyrrolidone product is accomplished by solution an organic solvent such as ethyl acetate, ether, cyclohexane, chloroform, petroleum ether, hexane, carbon disulfide, or carbon tetrachloride. Preferably the product is dissolved in carbon tetrachloride. This solution is extracted multiple times with water. $Na_2SO_4$ is added to remove traces of water from the organic solution. The solid $Na_2SO_4$ is removed by filtration. The organic solvent is evaporated to recover the pure monomer.

The homopolymer is synthesized by dissolving a free radical initiator in a monomer of formula I above. The initiator may be benzoyl peroxide, azobisisobutyronitrile, or any as would occur to one skilled in the art. Preferably the initiator is azobisisobutyronitrile. Preferably the monomer is N-isopropyl-3-methylene-2-pyrrolidone. The resulting mixture is heated for from about 15 to about 50 hours at from about 50° to about 70° C. Preferably the mixture is heated for from 22 to 26 hours at from 55°–65° C.

A copolymer is synthesized by mixing a monomer of formula I above with an acrylate or methacrylate such as 2-hydroxyethyl methacrylate, methylethylmethacrylate, ethylmethacrylate, ethylacrylate, a vinyl polymer, a vinyl alcohol, vinylacetate, or vinylpyrrolidone. Preferably 2-hydroxyethyl methacrylate is used.

A free radical initiator such as benzoyl peroxide or azobisisobutyronitrile is then dissolved in the mixture. Preferably azobisisobutyronitrile is used. The mixture is heated to about 50° to about 70° C. for about 15 to 50 hours to produce a polymer film and then soaked in water to remove unreacted monomer and any other impurities. Preferably the mixture is heated to about 55° to about 65° C. for about 22 to about 26 hours. The copolymer swells but does not dissolve in the water.

The water insoluble copolymer was evaluated as a drug delivery system. Permeability coefficients of the model drug diphenhydramine were determined.

It was found that a copolymer of N-isopropyl-3-methylene-2-pyrrolidone with 2-hydroxyethyl methacrylate (HEMA) exhibits an equilibrium water concentration of 36.5% at room temperature. The permeability coefficient of diphenhydramine hydrochloride through the copolymer is $5.6 \times 10^{-8}$ cm$^2$/sec.

By way of comparison poly(hydroxyethyl methacrylate) (p-HEMA) exhibits an equilibrium water concentration of 40% at room temperature. The permeability coefficient of diphenhydramine hydrochloride through p-HEMA is $2.1 \times 10^{-7}$ cm$^2$/sec.

In the present invention the copolymers are used to provide unique hydrogels which swell but do not dissolve in the presence of water. Hydrogels are advantageous because of their good biocompatibility. As such these new polymers have wide application in pharmaceutical areas. For example, they can be used for coating solid dosage forms such as tablets, pellets, implant devices, or other materials used as a matrix to provide for a controlled release of medicaments.

The forms are for different routes of administration as would occur to a skilled practitioner. Preferable routes are oral, buccal, sublingual, vaginal, rectal, and the like.

The copolymers of the instant invention have utility in transdermal delivery systems which provide controlled release of a medicament. The property of swelling but not dissolving overcomes a problem found in many transdermal devices. The copolymers of the present invention are biocompatible as they provide a nonocclusive material for the skin. The copolymer readily absorbs perspiration as it is released by the skin.

Virtually any pharmaceutical suitable for transdermal administration can be used. Useful pharmaceuticals include but are not limited to: antihistaminics, i.e., diphenhydramine, coronary drugs, i.e., nitroglycerin; estrogens; contraceptives; anesthetics, i.e., ketamine; analgesics, i.e., oxymorphone; antirheumatics; anticholinergics; cognition activators and other pharmaceuticals as would occur to one skilled in the art.

The copolymers also provide an excellent material for soft contact lenses as they are transparent, permeable to oxygen and biocompatible.

The copolymers of the instant invention are also useful as wound dressing materials as the materials provide for easy removal of the dressing. Furthermore, they are biocompatible with an open wound and are capable of absorbing moisture.

The following examples illustrate how the polymers are produced. They are not intended to in any way limit the scope of the invention.

EXAMPLE 1

Synthesis of Monomer, N-isopropyl-3-methylene-2-pyrrolidone

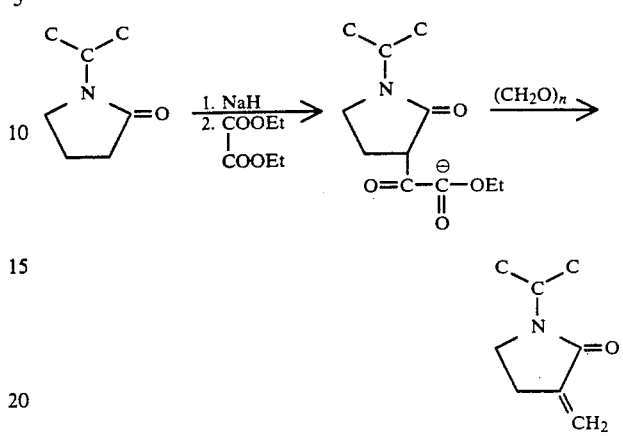

1. In a 1 liter round bottom flask, 67.75 ml diethyl oxalate (0.5 mole), 19.5 g sodium hydride (0.65 mole), and 600 ml of ether were added.
2. To this mixture, 49.3 ml of N-isopropyl-2-pyrrolidone (0.5 mole) was added.
3. Following reflux overnight, the mixture was stirred for about 18 hours at room temperature.
4. The resulting yellow solid (adduct of N-isopropyl-2-pyrrolidone with diethyl oxalate) was filtered and dried. (Yield was 80 g, 72%.)
5. The yellow solid was suspended in 500 ml xylene.
6. 16 g of paraformaldehyde was added to the suspension.
7. The mixture was heated 1 hour at 100°–110° C. and refluxed for 1 hour after adding 1 g of CuCl.
8. The whole mixture was cooled to room temperature and filtered.
9. An additional 0.1 g of CuCl was added to the filtrate.
10. The filtrate was vacuum distilled.
11. The fraction which distilled at 55°–65° C. and 0.3 mmHg was collected (18.4 g).
12. HPLC analysis of the fraction showed that the product contained 67% of N-isopropyl-3- methylene-2-pyrrolidone and 33% of the starting material (N-isopropyl-2-pyrrolidone).

EXAMPLE 2

Purification of N-Isopropyl-3-Methylene-2-Pyrrolidone by Extraction 1. 18.4 g of N-isopropyl-3-methylene-2-pyrrolidone containing about 33% of impurity (N-isopropyl-2-pyrrolidone) was dissolved in 100 ml CCl$_4$.
2. This solution was extracted five times with 100 ml of water each time.
3. Trace amounts of water in the organic solution were removed by addition of Na$_2$SO$_4$ and allowed to stand overnight.
4. The solid Na$_2$SO$_4$ was removed by filtration and the organic solvent was evaporated to recover pure monomer.
5. This monomer was analyzed by HPLC. The purity of the compound was 97%.
6. NMR and mass spectra confirmed the structure of the compound. The compound was N-isopropyl-3-methylene-2-pyrrolidone.

EXAMPLE 3

Synthesis of Homopolymer of N-Isopropyl-3-Methylene-2-Pyrrolidone 1. 0.006 g of azobisisobutyronitrile was dissolved in 2 g of the monomer.
2. The mixture was heated for 24 hours at 60° C.
3. The polymer thus formed was transparent and dissolved both in ethanol and in water.

EXAMPLE 4

Synthesis of Copolymer of N-Isopropyl-3-Methylene-2-Pyrrolidone with 2-Hydroxyethylmethacrylate 1. 5 g of N-isopropyl-3-methylene-2-pyrrolidone and 5 g of 2-hyrdoxy-ethyl methacrylate were mixed.
2. 0.03 g of azobisisobutyronitrile was dissolved in this mixture.
3. The mixture was transferred to a plastic mold.
4. The mold was heated to 60° C. for 24 hours to produce a polymer film.
5. This film was soaked in distilled water to remove unreacted monomer and other impurities.
6. The copolymer swelled, but did not dissolve in water.

We claim:

1. A method of using a copolymer of N-isopropyl-3-methylene-2-pyrrolidone and 2-hydroxyethylmethacrylate having an equilibrium water concentration of 36.5% by weight at room temperature in a transdermal delivery system for administration of a pharmaceutical.

2. A method of using a copolymer of N-isopropyl-3-methylene-2-pyrrolidone and 2-hydroxyethylmethacrylate having an equilibrium water concentration of 36.5% by weight at room temperature for sustained release dosage forms for administration of a pharmaceutical.

3. A method of using a copolymer of N-isopropyl-3-methylene-2-pyrrolidone and 2-hydroxyethylmethacrylate having an equilibrium water concentration of 36.5% by weight at room temperature in a soft contact lens.

4. A method of using a copolymer of N-isopropyl-3-methylene-2-pyrrolidone and 2-hydroxyethylmethacrylate having an equilibrium water concentration of 36.5% by weight at room temperature as a wound dressing.

5. A sustained release pharmaceutical composition comprising a pharmaceutical in combination with a copolymer N-isopropyl-3-methylene-2-pyrrolidone and 2-hydroxyethylmethacrylate having an equilibrium water concentration of 36.5% by weight at room temperature.

* * * * *